United States Patent
Shoji et al.

(10) Patent No.: US 10,168,281 B2
(45) Date of Patent: Jan. 1, 2019

(54) MULTICOLOR FLUORESCENCE ANALYSIS DEVICE

(71) Applicant: HITACHI HIGH-TECHNOLOGIES CORPORATION, Tokyo (JP)

(72) Inventors: Tomohiro Shoji, Tokyo (JP); Junji Shiokawa, Tokyo (JP); Akihito Nishizawa, Tokyo (JP); Hirokazu Kato, Tokyo (JP); Junji Ishizuka, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/539,228

(22) PCT Filed: Nov. 11, 2015

(86) PCT No.: PCT/JP2015/081748
§ 371 (c)(1),
(2) Date: Jun. 23, 2017

(87) PCT Pub. No.: WO2016/121189
PCT Pub. Date: Aug. 4, 2016

(65) Prior Publication Data
US 2018/0011021 A1  Jan. 11, 2018

(30) Foreign Application Priority Data

Jan. 27, 2015 (JP) .................. 2015-013744

(51) Int. Cl.
*G01N 21/64* (2006.01)
*G01J 3/44* (2006.01)
(Continued)

(52) U.S. Cl.
CPC .............. *G01N 21/64* (2013.01); *G01J 3/36* (2013.01); *G01J 3/4406* (2013.01);
(Continued)

(58) Field of Classification Search
CPC ....... G01N 2021/6419; G01N 2021/64; G01N 2021/6421; G01N 2021/6471
See application file for complete search history.

(56) References Cited

U.S. PATENT DOCUMENTS

| | | | | |
|---|---|---|---|---|
| 2006/0017001 A1* | 1/2006 | Donders | ............ | G02B 21/0036 250/390.07 |
| 2011/0121204 A1* | 5/2011 | Kumazaki | ............ | G01N 21/648 250/459.1 |

(Continued)

FOREIGN PATENT DOCUMENTS

| | | |
|---|---|---|
| JP | 2001-198079 A | 7/2001 |
| JP | 2011-027706 A | 2/2011 |
| WO | 2014-013912 A1 | 1/2014 |

OTHER PUBLICATIONS

David R. Bentley et al.,"Accurate whole human genome sequencing using reversible terminator chemistry", Nature, Nov. 6, 2008, vol. 456.

(Continued)

*Primary Examiner* — Hugh H Maupin
(74) *Attorney, Agent, or Firm* — Mattingly & Malur, PC

(57) ABSTRACT

A multicolor fluorescence analysis device 11 is for detecting fluorescence emitted, as a result of excitation light irradiation, from a plurality of types of fluorophores included in a sample s, and is provided with an irradiation optical unit 520 for irradiating light emitted from a light source 510 onto a sample s as excitation light, a fluorescence condensation unit 530 having a fluorescence filter 531 that transmits light emitted from the sample s and transmits light of transmission wavelength bands different from the excitation wavelength bands, and a two-dimensional detector 554 that has a plurality of types of transmission filters 556 for transmitting prescribed wavelengths of light and detects the intensity of the light of the prescribed wavelength for each transmission filter 556, and the light emitted from at least two fluorophores from among the plurality of types of fluorophores is detected simultaneously and the fluorophore types are identified accordingly.

25 Claims, 11 Drawing Sheets

(51) Int. Cl.
*G01J 3/36* (2006.01)
*G01N 21/03* (2006.01)
*G01J 3/10* (2006.01)

(52) U.S. Cl.
CPC ...... *G01N 21/645* (2013.01); *G01J 2003/106* (2013.01); *G01N 21/0332* (2013.01); *G01N 2021/6419* (2013.01); *G01N 2021/6421* (2013.01); *G01N 2021/6441* (2013.01); *G01N 2021/6471* (2013.01)

(56) References Cited

U.S. PATENT DOCUMENTS

| | | |
|---|---|---|
| 2012/0097864 A1 | 4/2012 | Takahashi et al. |
| 2013/0258332 A1* | 10/2013 | Iga .......................... G01J 3/06 356/301 |
| 2014/0027653 A1 | 1/2014 | Reches et al. |

OTHER PUBLICATIONS

Jay Shendure et al., "Accurate Multiplex Polony Sequencing of an Evolved Bacterial Genome", Science Sep. 9, 2005, vol. 309, pp. 1728-1732.
International Search Report of PCT/JP2015/081748 dated Feb. 9, 2016.

* cited by examiner (a)

(b)

(c)

(d)

(e)

(f)

(g)

(h)

|  | B FILTER | G FILTER | R FILTER | IR FILTER |
|---|---|---|---|---|
| FIRST FLUORESCENT DYE | 0.35 | 1.00 | 0.14 | 0.03 |
| SECOND FLUORESCENT DYE | 0.12 | 1.00 | 0.54 | 0.12 |
| THIRD FLUORESCENT DYE | 0.11 | 0.33 | 1.00 | 0.63 |
| FOURTH FLUORESCENT DYE | 0.13 | 0.31 | 1.00 | 0.95 |

(a1)

(a2)

(b)

(c1)

|  | G' FILTER | R' FILTER |
|---|---|---|
| FIRST FLUORESCENT DYE | 1.00 | 0.10 |
| SECOND FLUORESCENT DYE | — | — |
| THIRD FLUORESCENT DYE | 0.81 | 1.00 |
| FOURTH FLUORESCENT DYE | — | — |

(c2)

|  | G' FILTER | R' FILTER |
|---|---|---|
| FIRST FLUORESCENT DYE | — | — |
| SECOND FLUORESCENT DYE | 1.00 | 0.45 |
| THIRD FLUORESCENT DYE | — | — |
| FOURTH FLUORESCENT DYE | 0.04 | 1.00 |

MULTICOLOR FLUORESCENCE ANALYSIS DEVICE

TECHNICAL FIELD

The present invention relates to a multicolor fluorescence analysis device.

BACKGROUND ART

For example, in a biological test, there is known an analysis device of collectively irradiating a large number of minute DNA fragments labeled with fluorescent dyes with excitation light, detecting fluorescence emitted from the fluorescent dyes, and deciphering a base sequence of each DNA fragment (for example, refer to NPL 1).

In the above-described analysis device, the DNA fragments are arranged at a high density in a reaction vessel called a flow cell, and bases complementary to the bases of DNA fragments of the four types of bases labeled with different fluorescent dyes are incorporated into the DNA fragment by using a polymerase chain reaction (PCR), and the bases are specified by identifying the fluorescent dyes by irradiation with excitation light. By repeating this operation, the base sequence is deciphered.

In addition, related to this, there is disclosed a method for obtaining sequence information of each DNA fragment by performing PCR on microparticles by using the microparticles (DNA beads) as a carrier carrying DNA fragments, scattering and fixing the microparticles on a glass substrate, and on the glass substrate, performing an enzymatic reaction (ligation), incorporating a substrate added with fluorescent dyes, and detecting fluorescence (for example, refer to NPL 2).

In such analysis devices, it is expected that the speed of deciphering the base sequence can be improved in that a large number of DNA fragments can be analyzed in parallel.

CITATION LIST

Patent Literature

NPL 1: D. R. Bentley et al., Accurate whole human genome sequencing using reversible terminator chemistry, Nature 456, 53-59, (2008)
NPL 2: Science 2005, vol. 309, p. 1728-1732

SUMMARY OF INVENTION

Technical Problem

However, in a case where fluorescent analysis is performed on a sample containing different fluorescent dyes as typified by the above-described deciphering of the base sequence of DNA, in an analysis device of the related art, since the analysis is performed while switching filters transmitting fluorescence emitted from the fluorescent dyes for each fluorescent dye to be measured, it takes time for the switching, and thus, it takes time to perform the analysis, so that it cannot be said that current demand is necessarily satisfied in terms of speeding up the analysis.

The present invention is contrived under the above-described circumstances, and an object of the present invention is to provide a multicolor fluorescence analysis device capable of rapidly and reliably identifying fluorescence emitted from a plurality of types of fluorescent dyes having different fluorescent wavelengths.

Solution to Problem

The present invention relates to:
(1) a multicolor fluorescence analysis device for detecting fluorescence emitted from a plurality of types of fluorescent dyes having different fluorescence wavelengths contained in a sample by irradiation with excitation light, the multicolor fluorescence analysis device including: a light source for excitation; an irradiation optical unit having an excitation filter that transmits light in a plurality of different excitation wavelength bands and irradiating the sample with light emitted from the light source as the excitation light through the excitation filter; a fluorescence condensation unit having a fluorescence filter that transmits at least a portion of the fluorescence emitted from the sample by the irradiation of the excitation light and transmits light in a plurality of transmission wavelength bands not including the excitation wavelength band; and a two-dimensional detector having a plurality of types of transmission filters that transmit light having a predetermined wavelength out of the light transmitted by the fluorescence filter and detecting an intensity of the light transmitted by each of the transmission filters for each of the transmission filters, wherein light emitted from at least two types of fluorescent dyes out of the plurality of types of fluorescent dyes is simultaneously detected by using the two-dimensional detector, and the types of the fluorescent dyes are identified from intensities of the detected light;
(2) the multicolor fluorescence analysis device according to (1), wherein the types of the transmission filters are four types;
(3) the multicolor fluorescence analysis device according to (1), wherein the types of the transmission filters are two types;
(4) a multicolor fluorescence analysis device for detecting fluorescence emitted from a plurality of types of fluorescent dyes having different fluorescence wavelengths contained in a sample by irradiation with excitation light, the multicolor fluorescence analysis device including: a light source for excitation; an irradiation optical unit having a plurality of excitation filters that transmit light in a plurality of different excitation wavelength bands and are switchable and irradiating the sample with light emitted from the light source as the excitation light through the excitation filter; a fluorescence condensation unit having a fluorescence filter that transmits at least a portion of the fluorescence emitted from the sample by the irradiation of the excitation light and transmits light in a plurality of transmission wavelength bands not including the excitation wavelength band; and a two-dimensional detector having a plurality of types of transmission filters that transmit light having a predetermined wavelength out of the light transmitted by the fluorescence filter and detecting an intensity of the light transmitted by each of the transmission filters for each of the transmission filters, wherein light emitted from at least two types of fluorescent dyes out of the plurality of types of fluorescent dyes is simultaneously detected by using the two-dimensional detector, and the types of the fluorescent dyes are identified from intensities of the detected light;
(5) the multicolor fluorescence analysis device according to (4), wherein the types of the transmission filters are four types;
(6) the multicolor fluorescence analysis device according to (4), wherein the types of the transmission filters are two types;

(7) a multicolor fluorescence analysis device for detecting fluorescence emitted from a plurality of types of fluorescent dyes having different fluorescence wavelengths contained in a sample by irradiation with excitation light, the multicolor fluorescence analysis device including: a plurality of light sources for excitation; an irradiation optical unit having an excitation filter that is provided for each of the light sources to transmit light in a plurality of different excitation wavelength bands and irradiating the sample with light emitted from the light source as the excitation light through the excitation filter; a fluorescence condensation unit having a fluorescence filter that transmits at least a portion of the fluorescence emitted from the sample by the irradiation of the excitation light and transmits light in a plurality of transmission wavelength bands not including the excitation wavelength band; and a two-dimensional detector having a plurality of types of transmission filters that transmit light having a predetermined wavelength out of the light transmitted by the fluorescence filter and detecting an intensity of the light transmitted by each of the transmission filters for each of the transmission filters, wherein one of the plurality of light sources is turned on to simultaneously detect light emitted from at least two types of fluorescent dyes out of the plurality of types of fluorescent dyes by using the two-dimensional detector, and the types of the fluorescent dyes are identified from intensities of the detected light;

(8) the multicolor fluorescence analysis device according to (7), wherein the types of the transmission filters are four types;

(9) the multicolor fluorescence analysis device according to (7), wherein the types of the transmission filters are two types;

(10) a multicolor fluorescence analysis device for detecting fluorescence emitted from a plurality of types of fluorescent dyes having different fluorescence wavelengths contained in a sample by irradiation with excitation light, the multicolor fluorescence analysis device including: a light source for excitation; an irradiation optical unit having an excitation filter that transmits light in a plurality of different excitation wavelength bands and irradiating the sample with light emitted from the light source as the excitation light through the excitation filter; a fluorescence condensation unit having a fluorescence filter that transmits at least a portion of the fluorescence emitted from the sample by the irradiation of the excitation light and transmits light in a plurality of transmission wavelength bands not including the excitation wavelength band; a splitting unit splitting the light transmitted by the fluorescence filter into two at a predetermined ratio for each wavelength; a first two-dimensional detector having a plurality of types of first transmission filters that transmit light having a predetermined wavelength out of one of the two lights split by the splitting unit and detecting an intensity of the light transmitted by each of the first transmission filters for each of the first transmission filters; and a second two-dimensional detector having a plurality of types of second transmission filters that transmit light having a predetermined wavelength out of the other of the two lights split by the splitting unit and detecting an intensity of the light transmitted by each of the second transmission filters for each of the second transmission filters, wherein light emitted from at least two types of fluorescent dyes out of the plurality of types of fluorescent dyes is simultaneously detected by using the first and second two-dimensional detectors, and the types of the fluorescent dyes are identified from intensities of the detected light;

(11) the multicolor fluorescence analysis device according to (10), wherein the types of the first and second transmission filters are four types, respectively;

(12) the multicolor fluorescence analysis device according to (10), wherein the types of the first and second transmission filters are two types, respectively;

(13) the multicolor fluorescence analysis device according to any one of (10) to (12), wherein the splitting unit has a dichroic mirror that transmits a portion of the light transmitted by the fluorescence filter and reflects the remaining portion, and transmittance of the light transmitted by the dichroic mirror changes substantially from 0% to 100% in a predetermined wavelength range;

(14) the multicolor fluorescence analysis device according to any one of (1) to (13), wherein the excitation light to be irradiated on the sample includes at least two excitation wavelength bands;

(15) the multicolor fluorescence analysis device according to any one of (1) to (14), wherein the excitation light to be irradiated on the sample includes at least three excitation wavelength bands; and

(16) the multicolor fluorescence analysis device according to anyone of (1) to (15), further including a data processing unit identifying two or more types of fluorescent dyes from the intensity of light detected by the two-dimensional detector.

Advantageous Effects of Invention

The present invention can provide a multicolor fluorescence analysis device capable of quickly and reliably identifying fluorescence emitted from a plurality of types of fluorescent dyes having different fluorescence wavelengths. Therefore, the multicolor fluorescence analysis device can be appropriately used for fluorescence analysis of living body-related substances such as DNAs and RNAs labeled with fluorescent dyes.

DESCRIPTION OF EMBODIMENTS

Figure 1:
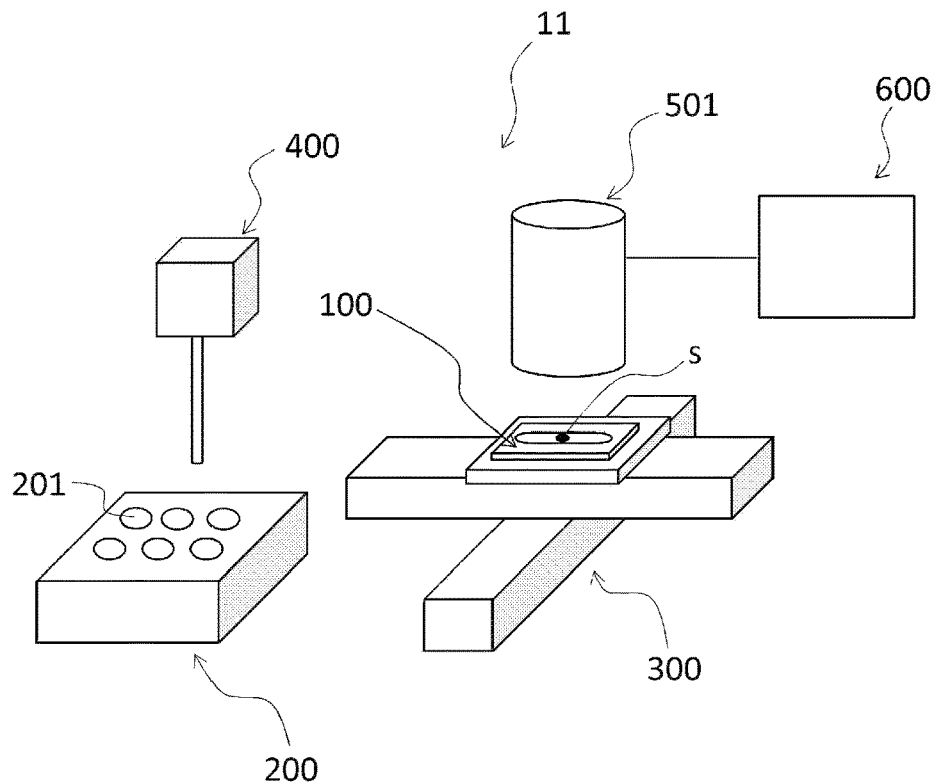
FIG. 1 is a schematic perspective view illustrating a multicolor fluorescence analysis device according to a first embodiment of the present invention.

The present invention is a multicolor fluorescence analysis device for detecting fluorescence emitted from a plurality of types of fluorescent dyes having different fluorescence wavelengths contained in a sample by irradiation with excitation light and identifying the type of fluorescent dyes from intensities of light detected by a two-dimensional detector described later.

Hereinafter, the multicolor fluorescence analysis device according to the present invention will be described with reference to the drawings, but the present invention is not limited to only the embodiments described in the drawings. In addition, in each embodiment described below, an example where a sample is microparticles (hereinafter, referred to as "DNA beads") carrying amplified clone DNA fragments to be analyzed and a multicolor fluorescence analysis device is used for deciphering a base sequence of the DNA fragments (DNA sequencer for identifying each base of A (adenine), G (guanine), C (cytosine) and T (thymine)) will be described.

In addition, four types of fluorescent dyes (first to fourth fluorescent dyes) for identifying each of the above-mentioned bases are not particularly limited as long as the bases can be identified. In first to fifth embodiments of the present specification, as the four types of fluorescent dyes, a first fluorescent dye (maximum absorption wavelength: 490 nm, maximum fluorescence wavelength: 515 nm), a second fluorescent dye (maximum absorption wavelength: 555 nm, maximum fluorescence wavelength: 565 nm), a third fluorescent dye (maximum absorption wavelength: 595 nm, maximum fluorescence wavelength: 615 nm), and a fourth fluorescent dye (maximum absorption wavelength: 650 nm, maximum fluorescence wavelength: 665 nm) are used.

In the second to fifth embodiments, a flow cell, a reagent container, a transport unit, a liquid feeding unit, and a data processing unit are the same as those of a first embodiment described below, and thus, in the second to fifth embodiments, the detailed description thereof will be omitted.

First Embodiment

FIG. 1 is a schematic perspective view illustrating a multicolor fluorescence analysis device according to a first embodiment of the present invention. As illustrated in FIG. 1, the multicolor fluorescence analysis device 11 is schematically configured to include a flow cell 100, a reagent container 200, a transport unit 300, a liquid feeding unit 400, an optical unit 501, and a data processing unit 600.

Figure 2:
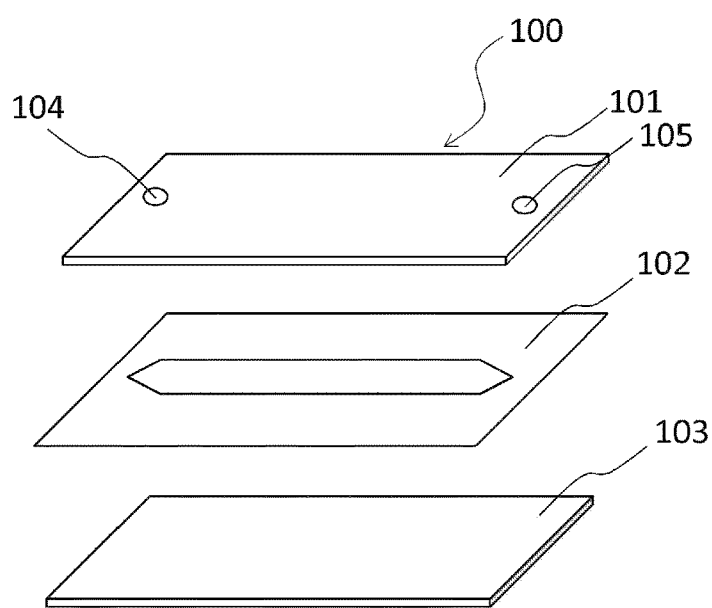
FIG. 2 is a schematic exploded perspective view illustrating an example of a flow cell in the multicolor fluorescence analysis device of FIG. 1.

As illustrated in FIG. 2, the flow cell 100 is configured with an upper substrate 101, a lower substrate 103, and an inner layer portion 102 interposed between the upper substrate 101 and the lower substrate 103.

The upper substrate 101 is a light-transmitting substrate subjected to surface treatment for adsorbing DNA beads on an inner plate surface thereof. Herein, the light-transmitting substrate denotes a substrate having a property capable of transmitting excitation light and light such as fluorescence emitted from DNA beads. Generally, fluorescence emitted from fluorescent dyes incorporated in living body-related substances such as DNA or RNA has a large amount of visible light. Therefore, in a case where the multicolor fluorescence analysis device 11 is used for the living body-related substances, it is preferable that the upper substrate 101 has a light-transmitting property with respect to visible light. As a material of the upper substrate 101, there may be exemplified a glass, an acrylic resin, a polycycloolefin resin, and the like. In addition, the upper substrate 101 is provided with an injection port 104 for injecting a reagent or the like and a discharge port 105 for discharging a used reagent or the like.

The reagent container 200 is a unit for storing reagents and the like used in a DNA sequencer. A plurality of storage containers 201 are usually provided in the reagent container 200, and reagents and the like are stored in each container for storage 201.

Figure 3:
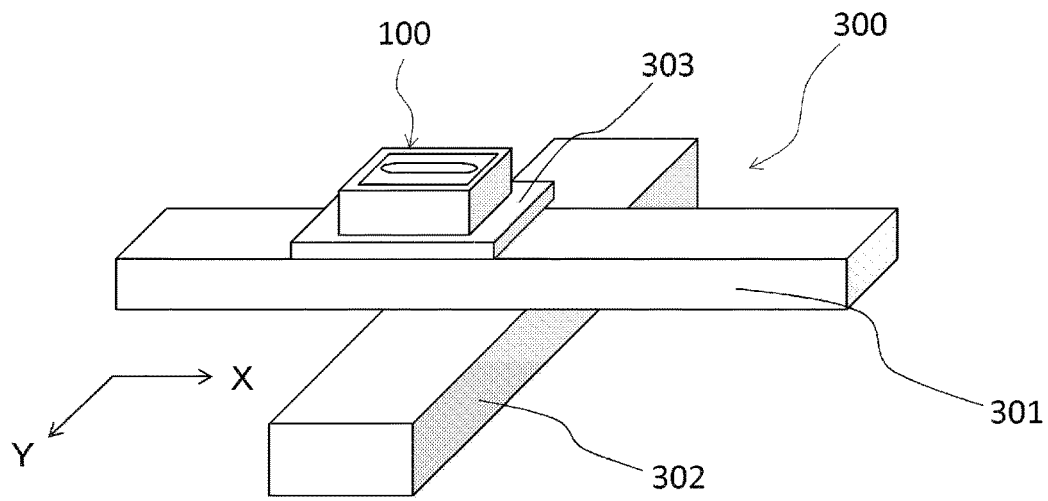
FIG. 3 is a schematic perspective view illustrating an example of a transport unit in the multicolor fluorescence analysis device of FIG. 1.

The transport unit 300 is a unit that transports the flow cell 100. As illustrated in FIG. 3, the transport unit 300 is configured to include a linear actuator 301 that is movable in the X-axis direction, a linear actuator 302 that is connected to the linear actuator 301 and movable in the Y-axis direction perpendicular to the X-axis direction, and a flow cell fixing base 303 that is connected to the linear actuator 301. The flow cell fixing base 303 is provided with a means (not illustrated) for fixing the flow cell 100. In addition, the flow cell fixing base 303 is provided with a temperature control means (not illustrated) for controlling the temperature of the flow cell 100.

Figure 4:
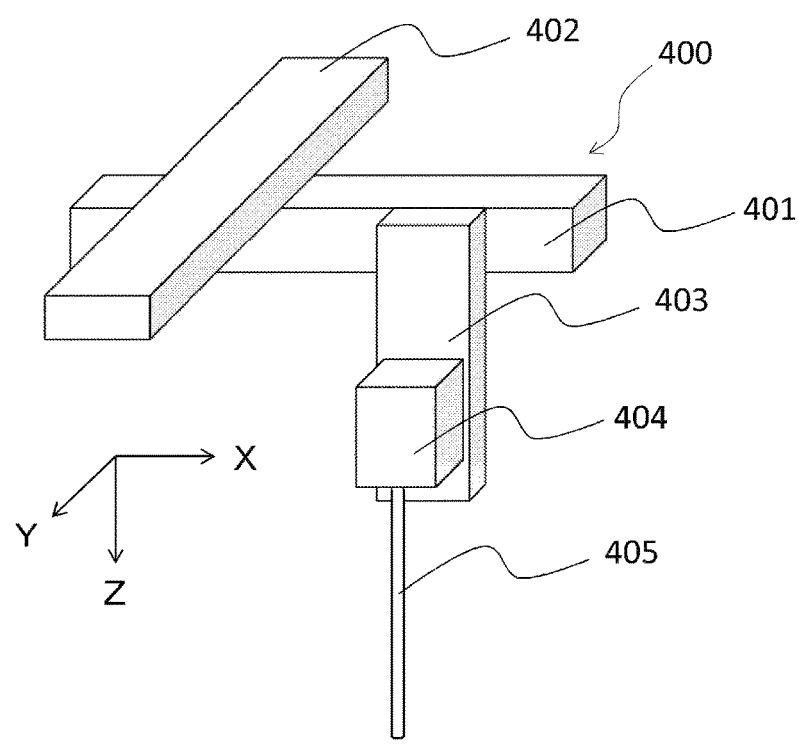
FIG. 4 is a schematic perspective view illustrating an example of a liquid feeding unit in the multicolor fluorescence analysis device of FIG. 1.

The liquid feeding unit 400 is a unit that supplies reagents and the like into the flow cell 100. As illustrated in FIG. 4, the liquid feeding unit 400 is configured to include a linear actuator 401 that is movable in the X axis direction in the horizontal plane, a linear actuator 402 that is connected to the linear actuator 401 and movable in the Y axis direction in the horizontal plane perpendicular to the X axis direction, a linear actuator 403 that is connected to the linear actuator 401 and movable in the vertical direction (Z axis direction), a dispensing nozzle 405, and a slider 404 that connects the dispensing nozzle 405 and the linear actuator 403.

The dispensing nozzle 405 is a pipe-shaped member. The dispensing nozzle 405 is connected to a syringe through piping (not illustrated). The dispensing nozzle 405 can three-dimensionally move by driving the above-described linear actuators 401, 402, and 403, so that, by manipulating a plunger (not illustrated) of the syringe, the reagent can be sucked from the storage container 201 and the reagent can be injected (supplied) into the flow cell 100 through the injection port 104 (refer to FIG. 2).

Figure 5:
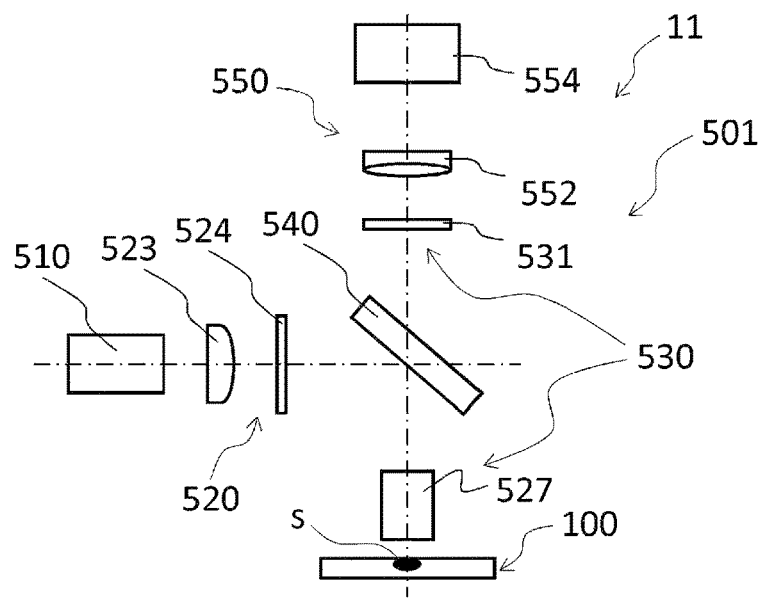
FIG. 5 is a schematic front view illustrating an example of an optical unit in the multicolor fluorescence analysis device of FIG. 1.

The optical unit 501 is a unit that irradiates a sample containing a fluorescent dye with excitation light and detects the fluorescence by performing spectroscopy on the obtained light. As illustrated in FIG. 5, the optical unit 501 is configured to include a light source 510, an irradiation optical unit 520, a fluorescence condensation unit 530, and a two-dimensional detection unit 550.

The light source 510 is a light source for excitation. The light source 510 emits light that is used to generate excitation light. The light source 510 is preferably a white light source. As a result, it is possible to reliably obtain excitation light having a desired wavelength band over the entire visible light range. The light source 510 is preferably a xenon short arc lamp or a white LED lamp. Since such a light source has a good continuous spectrum over the visible light range, such a light source is appropriate as a light source for generating light in a plurality of excitation wavelength bands.

The irradiation optical unit 520 has an excitation filter that transmits light in a plurality of different excitation wavelength bands and irradiates the sample s with the light emitted from the light source through the excitation filter as excitation light. The irradiation optical unit 520 is configured to include a collimating lens 523, an excitation filter 524, a dichroic mirror 540, and an objective lens 527.

The collimating lens 523 is a lens that adjusts the light emitted from the light source 510 to obtain collimated light (parallel light). The excitation filter 524 is a filter that transmits light in a plurality of different excitation wavelength bands out of the light emitted from the light source 510. As the excitation filter 524, an excitation filter obtained by forming a dielectric multilayer film on a light-transmitting glass is preferred from the viewpoint of reliable identification of the transmission wavelength region. The dichroic mirror 540 is a mirror that reflects excitation light and transmits fluorescence. The dichroic mirror 540 is configured to include a light-transmitting substrate such as glass and a wavelength selective transmitting film formed on the substrate and configured with a dielectric multilayer film that reflects light in a predetermined wavelength region and transmits light in another wavelength region. The objective lens 527 is a lens that condenses the excitation light transmitted by the excitation filter 524 to the measurement site of the sample s.

Figure 7A:
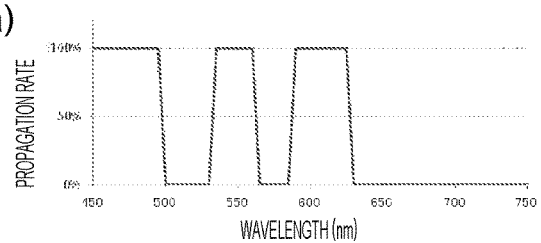
FIG. 7A is a schematic view illustrating an example of wavelength characteristics in the multicolor fluorescence analysis device of FIG. 1, in which (a) illustrates a wavelength characteristic (propagation rate) of excitation light to be irradiated on a sample, (b) illustrates an absorption spectrum of each fluorescent dye, (c) illustrates an absorption spectrum of each fluorescent dye by irradiation with excitation light, and (d) illustrates a fluorescence spectrum of each fluorescent dye.
Figure 7A:
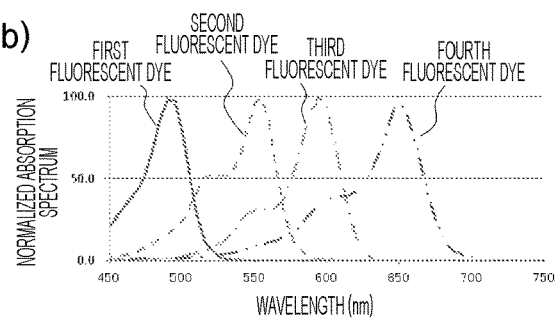
Figure 7A:
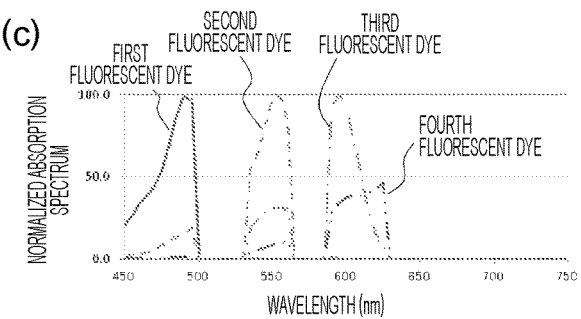
Figure 7A:
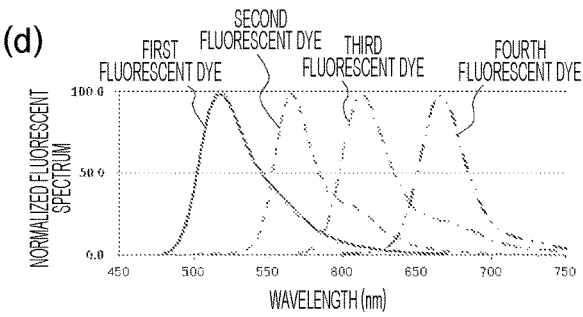

In addition, FIG. 7A(a) illustrates wavelength characteristics (propagation rate) of the excitation light to be irradiated on the sample s by using the excitation filter 524 and the dichroic mirror 540.

The fluorescence condensation unit 530 has a fluorescence filter that transmits at least a portion of the fluorescence emitted from the sample by the irradiation of the excitation light and transmits the light in a plurality of transmission wavelength bands not including the excitation wavelength band. The fluorescence condensation unit 530 is configured to include an objective lens 527 and a fluorescence filter 531.

The objective lens 527 is a lens that condenses the light emitted from the sample s. In addition, since the objective lens 527 in the irradiation optical unit 520 and the objective lens 527 in the fluorescence condensation unit 530 can be configured by commonly using the above-described dichroic mirror 540, in the embodiment, the irradiation optical unit 520 and the fluorescence condensation unit 530 are configured by using the same objective lens.

The fluorescence filter 531 is a filter that transmits at least a portion of the fluorescence emitted from the sample s and transmits light in a plurality of transmission wavelength bands not including the excitation wavelength band. Namely, the transmission wavelength band of the fluorescence filter 531 is set to such a wavelength band through which the reflected light of the excitation light is not transmitted. The light emitted from the sample s includes the fluorescence emitted from the fluorescent dye contained in the sample s by the irradiation of the excitation light and the reflected light of the excitation light reflected by the sample s. Therefore, the fluorescence filter 531 is used for the purpose of removing the reflected light of the excitation light so that the weak fluorescence emitted from the fluorescent dye does not fade away in the reflected light of the excitation light having the intensity significantly higher than the intensity of the fluorescence and the fluorescence can be reliably detected. As the fluorescence filter 531, a fluorescence filter obtained by forming a dielectric multilayer film on a light-transmitting glass is preferred from the viewpoint of reliable identification of the transmission wavelength region. The light obtained by removing light such as the excitation light by the transmission of the fluorescence filter 531 is transmitted to the two-dimensional detection unit 550 described later.

The two-dimensional detection unit 550 detects the fluorescence emitted from the sample s. The two-dimensional detection unit 550 is configured to include a tube lens 552 and a two-dimensional detector 554.

The tube lens 552 is a lens that condenses the light transmitted by the fluorescence filter 531 and forms an image of the condensed light on a two-dimensional image sensor (not illustrated) of the two-dimensional detector 554 described later.

The two-dimensional detector 554 is configured to include a plurality of types of transmission filters that transmit light having a predetermined wavelength out of the light transmitted by the fluorescence filter, and detects the intensity of light transmitted by the transmission filter for each transmission filter. The two-dimensional detector 554 is a single-plate camera which splits the light transmitted by the fluorescence filter 531 into a plurality of different wavelength bands. The two-dimensional detector 554 is configured to include a plurality of types of transmission filters 556 and a two-dimensional image sensor.

Figure 6:
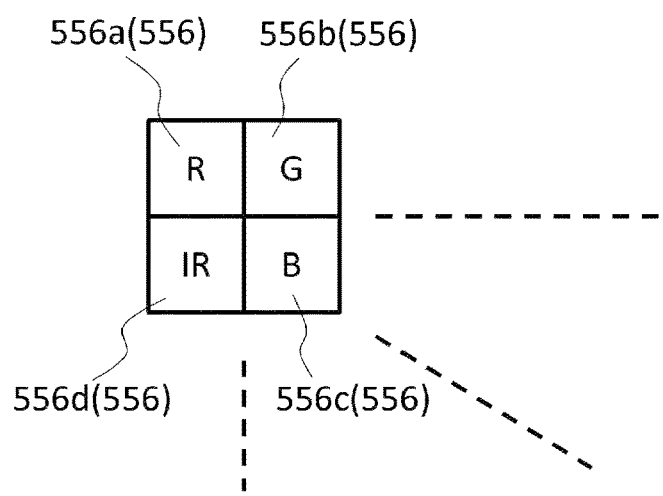
FIG. 6 is a schematic view illustrating an arrangement of transmission filters of a two-dimensional detector in the multicolor fluorescence analysis device of FIG. 1.

Each of the transmission filters 556 is a filter that transmits light having a predetermined wavelength out of the light transmitted by the fluorescence filter 531. In the embodiment, the types of the transmission filter 556 include four types having different transmission wavelength bands. As illustrated in FIG. 6, the above-mentioned four types of transmission filters include an R filter (filter mainly transmitting light in the red region) 556a, a G filter (filter mainly transmitting light in the green region) 556b, a B filter (filter mainly transmitting light in the blue region) 556c, and an IR filter (filter mainly transmitting light in the near infrared region) 556d. The four types of transmission filters are arranged by setting a block where one R filter 556a, one G filter 556b, one B filter 556c, and one IR filter 556d are aligned one by one as one unit and repeating the unit in a plane direction. In addition, from the viewpoint of improvement of spatial resolution, each of the transmission filters 556 is provided to each detection element (element for measuring the intensity of incident light, not illustrated) of the two-dimensional image sensor described later so as to correspond to each detection element.

The two-dimensional image sensor is a sensor that detects the intensity of light having a predetermined wavelength transmitted by the transmission filter 556 for each transmission filter 556. In the two-dimensional image sensor, a large number of detection elements are arranged in a lattice pattern, and the intensity of light is detected for each detection element. As the two-dimensional image sensor, for example, a monochrome CCD, a CMOS sensor, or the like can be adopted.

In such an optical unit 501, the light emitted from the light source 510 is condensed by the collimating lens 523. The light in a specific wavelength band out of the collected light is transmitted by the excitation filter 524 as excitation light. Furthermore, the light in a specific wavelength band out of the excitation light transmitted by the excitation filter 524 is reflected by the dichroic mirror 540 and is condensed by the objective lens 527 to the region where the DNA beads (sample s) are captured. Herein, the wavelength band which is transmitted by the excitation filter 524 and is reflected by the dichroic mirror 540 includes a plurality of wavelength bands necessary for exciting all of the plurality of types of fluorescent dyes contained in the DNA fragment.

The fluorescence emitted from plurality of types of fluorescent dyes excited by irradiating the sample s with the excitation light is condensed by the objective lens 527 passes through the dichroic mirror 540 that transmits light in a specific wavelength band and through the fluorescence filter 531 that transmits light in a predetermined wavelength band, and is formed as an image on the two-dimensional image sensor of the two-dimensional detector 554 by the tube lens 552. The image-formed fluorescence is spectroscopically-split by various transmission filters 556, and the intensity of the spectroscopically-split light is measured by a detection element provided for each transmission filter 556. In addition, the wavelength band that is transmitted through the dichroic mirror 540 and the fluorescence filter 531 includes all or some of the wavelength bands of the fluorescence emitted from a plurality of the types of fluorescent dyes contained in the DNA fragment.

The data processing unit 600 is a unit configured with a data processing unit (not illustrated) identifying two or more types of fluorescent dyes from the intensity of the light detected by the two-dimensional detector 554. The data processing unit 600 acquires the detected fluorescence as two-dimensional image data and analyzes the two-dimensional image data to identify the fluorescent dyes contained in each sample s. As the data processing unit 600, for example, a personal computer or the like capable of analyzing the two-dimensional image data can be adopted.

In this manner, since the multicolor fluorescence analysis device 11 is configured to include the data processing unit, it is possible to analyze the two-dimensional image data of the detected fluorescence and to identify the fluorescent dyes contained in the sample s.

Next, in the first embodiment, a method of identifying the fluorescent dyes contained in the samples will be described. In addition, in the following description, for the convenience, it is assumed that characteristics (for example, characteristics of a spectrum of the light source 510, a spectral sensitivity of each detection element in the two-dimensional detector 554, and the like) other than optical elements are uniform in a wavelength range to be detected.

White light emitted from the light source 510 is irradiated on the sample s (DNA beads) as excitation light through the collimating lens 523, the excitation filter 524, the dichroic mirror 540, and the objective lens 527. The wavelength characteristic (propagation rate) of the irradiated excitation light is obtained by multiplying a wavelength characteristic (transmittance) of the excitation filter 524 by a wavelength characteristic (reflectance) of the dichroic mirror 540 and is expressed, for example, as illustrated in FIG. 7A(a).

Herein, a normalized absorption spectrum of the four types of fluorescent dyes (first to fourth fluorescent dyes) to be detected is the characteristic illustrated in FIG. 7A(b). Therefore, in order to excite all of the fluorescent dyes, excitation light including at least a portion of the absorption spectrum of the fluorescent dyes from the irradiation optical unit 520 is irradiated on the sample s for each of the four types of fluorescent dyes.

The normalized absorption spectrum exhibited by each fluorescent dye contained in the sample s by the irradiation of the excitation light becomes the characteristic illustrated in FIG. 7A(c). The absorption spectrum illustrated in FIG. 7A(c) is obtained by superposing the propagation rate illustrated in FIG. 7A(a) and the absorption spectrum illustrated in FIG. 7A (b). In addition, a degree of the energy of the excitation light absorbed by each fluorescent dye can be estimated from a value (area surrounded by the graph) obtained by integrating an absorption spectrum graph illustrated in FIG. 7A(c) with the wavelength.

Herein, the normalized fluorescence spectrum emitted from the above-mentioned four types of fluorescent dyes becomes the characteristic illustrated in FIG. 7A(d).

The light emitted from the sample s is incident on the two-dimensional detector 554 through the objective lens 527, the dichroic mirror 540, the fluorescence filter 531, and the tube lens 552. The light emitted from the sample s includes reflected light (hereinafter, also simply referred to as "reflected light") obtained by reflection of the excitation light by the sample s or the like in addition to the fluorescence emitted from the fluorescent dye. Since the reflected light has a very high intensity in comparison with the fluorescence as described above, the reflected light is removed before the incidence on the two-dimensional detection unit 550 so that the detection of the fluorescence by the two-dimensional detection unit 550 is not inhibited.

Figure 7B:
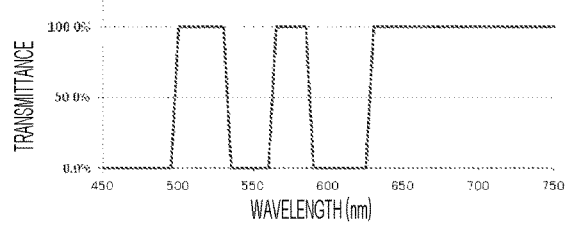
FIG. 7B is a schematic view illustrating an example of wavelength characteristics of the multicolor fluorescence analysis device of FIG. 1, in which (e) illustrates a wavelength characteristic (transmittance) by a dichroic mirror and a fluorescence filter, (f) illustrates a fluorescence spectrum of each fluorescent dye transmitting the fluorescence filter, (g) illustrates a wavelength characteristic (transmittance) of each of various transmission filters, and (h) illustrates an intensity ratio of each fluorescent dye for each transmission filter.
Figure 7B:
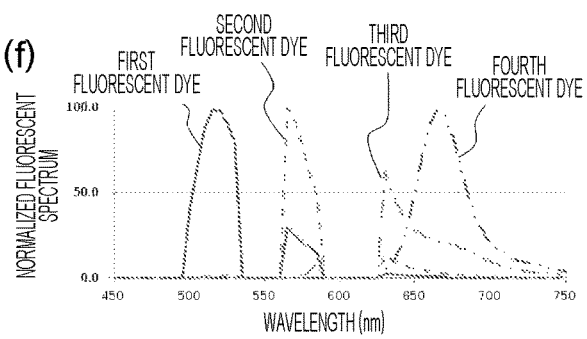
Figure 7B:
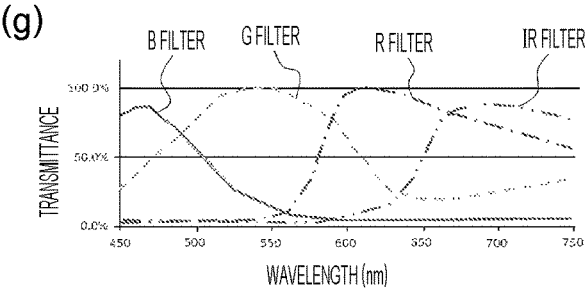

Herein, FIG. 7B(e) illustrates the wavelength characteristic (transmittance) obtained by superposing the wavelength characteristic (transmittance) of the dichroic mirror 540 and the wavelength characteristic (transmittance) of the fluorescence filter 531. The transmission wavelength characteristic of the fluorescence condensation unit 530 is a reverse characteristic of the wavelength characteristic of the excitation light of the irradiation optical unit 520 illustrated in FIG. 7A(a). Namely, in a wavelength band where the propagation rate of the excitation light in the irradiation optical unit 520 is about 100%, the transmittance of the fluorescence condensation unit 530 is designed to be about 0%. Therefore, the reflected light can be removed from the light emitted from the sample s, so that the reflected light can be prevented from being incorporated into the two-dimensional detection unit 550, and thus, the fluorescence can be reliably identified.

FIG. 7B(f) illustrates a superposition of the fluorescence spectrum illustrated in FIG. 7A(d) and the wavelength characteristic (transmittance) illustrated in FIG. 7B(e). The normalized fluorescence spectrum illustrated in FIG. 7B (f) substantially illustrates the fluorescence spectrum of each fluorescent dye that reaches the two-dimensional detection unit 550 after passing through the fluorescence condensation unit 530. As illustrated in FIG. 7B (f), the light reaching the two-dimensional detection unit 550 does not include almost any excitation light illustrated in FIG. 7A(c).

The light passing through the fluorescence condensation unit 530 is incorporated into the two-dimensional detection unit 550 and is spectroscopically-split by the transmission filter 556, and the intensity after the spectroscopy is measured by the two-dimensional image sensor. FIG. 7B(g) illustrates a transmission characteristic for each of the four types of transmission filters (the R filter 556*a*, the G filter 556*b*, the B filter 556*c*, and the IR filter 556*d*).

In the embodiment, since the above-described four types of transmission filters 556 are provided, the four types of fluorescence emitted from the respective fluorescent dyes are spectroscopically-split by the above-mentioned four types of transmission filters 556, respectively, and each intensity of the spectroscopically-split light is simultaneously measured by the detection element. In the data processing unit, the four types of fluorescent dyes are simultaneously identified from the fluorescence measured above. In this manner, since the transmission filters 556 are of four types, it is possible to reliably identify the types of fluorescent dyes from the ratio of the intensities of light detected by using the four types of transmission filters 556.

Herein, the intensity ratios of the fluorescence emitted from the respective fluorescent dyes detected by the respective detection elements are estimated as values in a table illustrated in FIG. 7B(h). Each value is calculated from an integral value of the spectrum obtained by superposing the fluorescence spectrum illustrated in FIG. 7B(f) and the wavelength characteristic (transmittance) for each of the various transmission filters illustrated in FIG. 7B(g). In addition, although the component of the G filter 556*b* in the light from the first and second fluorescent dyes is most strongly detected, since the intensity ratios of the components in the B filter 556*c* and the R filter 556*a* are different from each other, it is possible to determine the fluorescent dyes. In addition, although the component of the R filter 556*a* in the light from the third and fourth fluorescent dyes is most strongly detected, since the intensity ratio in the IR filter 556*d* is different, it is possible to determine the fluorescent dyes.

Herein, in order to explain the contents of the present invention, an example using specific fluorescent dyes or the like has been described. However, by optimizing characteristics of the fluorescent dyes and the optical elements to be used, more preferable conditions can be obtained. For example, the fluorescence emitted from DNA beads (sample s) has a spatial intensity distribution. Therefore, it is preferable to increase the imaging magnification (to increase the size of an image of the DNA beads on the two-dimensional image sensor relative to the size of the detection element) so that the influence thereof can be reduced down to a negligible level.

Figure 8:
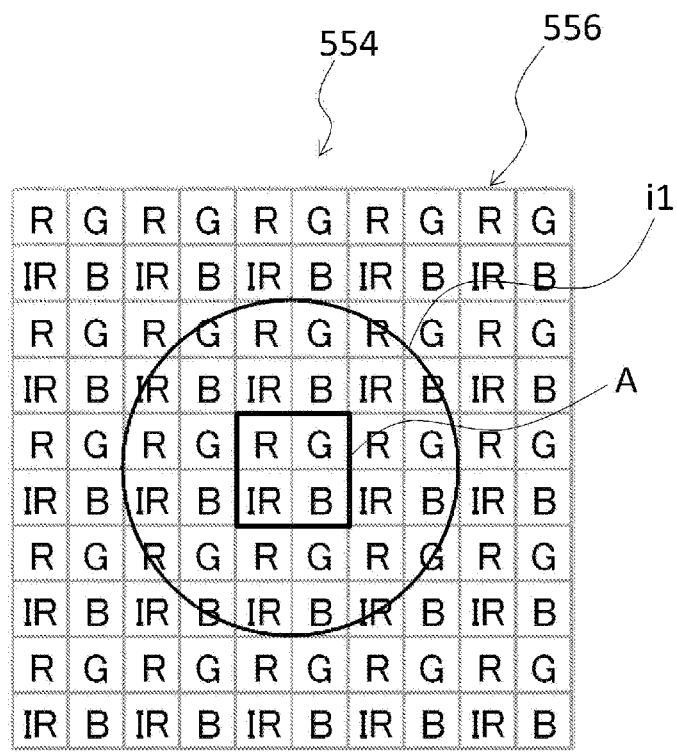
FIG. 8 is a schematic view illustrating an example of an image of DNA beads formed on a two-dimensional image sensor of the multicolor fluorescence analysis device of FIG. 1.

FIG. 8 is a schematic view illustrating an example of an image i1 of a DNA beads formed on the two-dimensional image sensor of the multicolor fluorescence analysis device 11 of FIG. 1. The figure illustrates an example where the imaging magnification of the optical unit 501 is about 20 times, the size of the detection element of the two-dimensional image sensor is 3 μm, and the projection size of the DNA beads is 0.9 μm in diameter (however, in the figure, the influence of aberration and imaging ability of the optical system and the like are not considered). In this example, the image i1 of the DNA beads is projected in the region of 6×6 pixels on the two-dimensional image sensor. In the measurement of the fluorescence, a region A including each of the R, G, B, and IR transmission filters 556 near the center within this region is extracted. At this time, if the spatial fluorescence intensity distribution in the region A is sufficiently small with respect to the intensity ratio, it is possible to identify the fluorescent dye from the intensity ratio obtained by each detection element within the region A. In this example, as illustrated in FIG. 7B(h), the difference in intensity ratio between the fluorescent dyes for the respective detection elements is about several tens %, and thus, if the spatial fluorescence intensity distribution is within 10%, is possible to identify the respective fluorescent dyes.

As described above, the irradiation optical unit 520 having the excitation filter 524 that transmits the light having a plurality of different excitation wavelength bands, the fluorescence condensation unit 530 having the fluorescence filter 531 that transmits the light in a plurality of transmission wavelength bands not including the excitation wavelength band, and the two-dimensional detector 554 having a plurality of types of transmission filters that transmit the light having a predetermined wavelength to detect the intensities of the light transmitted by the transmission filter for each transmission filter are provided, and since the two-dimensional detector 554 is used to simultaneously detect the light emitted from at least two types of fluorescent dyes out of a plurality of the types of fluorescent dyes, the multicolor fluorescence analysis device 11 can be quickly and reliably identify the fluorescence emitted from a plurality of the types of fluorescent dyes having different fluorescence wavelengths. Therefore, the multicolor fluorescence analysis device 11 can be appropriately used for fluorescence analysis for living body-related substances such as DNA and RNA labeled with fluorescent dyes. Hereinafter, an analysis method for a DNA base sequence by using the multicolor fluorescence analysis device 11 will be described.

The analysis method of the DNA base sequence by using the multicolor fluorescence analysis device 11 is not particularly limited, but for example, an analysis method of a DNA sequence by using a stepwise ligation method (Sequencing by Oligonucleotide Ligation and Detection) can be exemplified. The stepwise ligation method refers to a method of sequentially binding probes fluorescently labeled with fluorescent dyes using single-stranded DNAs bound to DNA beads in a flow cell as a template and determining the sequence in units of two bases.

As an enzymatic reaction by a ligase, oligonucleotides containing fluorescent dyes corresponding to a target sequence of a DNA fragment are bound, and an elongation reaction is allowed to occur. After completion of the elongation reaction, the excitation light is irradiated on the fluorescent dyes, and the fluorescence is detected by the optical unit 501. Thereafter, the fluorescent dyes are cut, the elongation reaction is further performed, and the fluorescence corresponding to the next sequence is detected.

By repeating the elongation reaction, the detection of fluorescence, and the cutting of fluorescent dyes as described above, the bases corresponding to the fluorescent dyes are sequentially determined and are finally deciphered as the base sequence of the DNA fragment. By this method, it is possible to decipher the bases of tens to hundreds of bp in one cycle, and it is possible to analyze the data of tens of Gb in one run. In such a stepwise ligation method, a plurality of DNA fragments in the flow cell 100 can be sequenced in parallel by repeatedly hybridizing fluorescently-labeled oligonucleotides with the fluorescent dyes.

Figure 16:
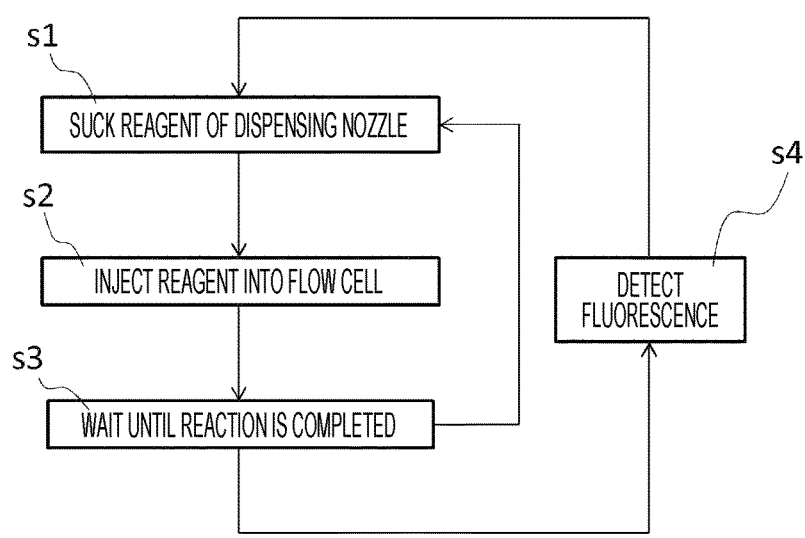
FIG. 16 is a flowchart illustrating an example of a base sequence determination procedure using the multicolor fluorescence analysis device of FIG. 1.

Next, one cycle of the base sequence determination procedure in the elongation reaction and the like described above will be described in detail. FIG. 16 is a flowchart illustrating an example of the base sequence determination procedure using the multicolor fluorescence analysis device 11 of FIG. 1. In the determination of the base sequence, first, the dispensing nozzle 405 of the liquid feeding unit 400 is inserted into the storage container 201 installed in the reagent container 200, and the reagent in the storage container 201 is sucked (step s1). Next, the liquid feeding unit 400 and the transport unit 300 are driven to inject the reagent into the flow cell 100 with the dispensing nozzle 405 communicating with the injection port 104 of the flow cell 100 (step s2).

Herein, in a case where temperature control is necessary, the reaction is performed while the temperature is controlled with a temperature control device (not illustrated) incorporated in the flow cell fixing base 303 of the transport unit 300, and the waiting state is maintained until the reaction is completed (step s3). In a case where a plurality of reaction steps are necessary, after the reaction steps are repeated, the fluorescent dyes are bound to the DNA fragment in the flow cell 100, so that the state where fluorescence detection is possible is obtained.

Next, the transport unit 300 is driven to move the flow cell 100 on the flow cell fixing base 303 right under the objective lens 527 of the optical unit 501, and the fluorescence detection of the sample s in the flow cell 100 is performed (step s4). In addition, in the fluorescence detection, if the area of the upper substrate 101 to which DNA fragments are fixed is larger than the area detectable by the optical unit 501, the transport unit 300 is driven to gradually move the flow cell fixing base 303 little by little and sequentially performing the fluorescence detection of the sample s within a predetermined range on the upper substrate 101 by two-dimensionally scanning. Next, the two-dimensional image data of the fluorescence detected in the optical unit 501 is transmitted as an electric signal to the data processing unit 600, and the data processing unit 600 analyses the data to identify the fluorescent dyes, so that the bases corresponding to the identified fluorescent dyes are determined.

In this manner, after the fluorescence detection for one cycle is performed, the next cycle is executed, and by repeating this, the bases corresponding to the fluorescent dyes are sequentially determined, and the base sequence of the DNA fragment is deciphered.

Second Embodiment

A multicolor fluorescence analysis device 12 according to a second embodiment is schematically configured to include a flow cell 100, a reagent container 200, a transport unit 300, a liquid feeding unit 400, an optical unit 502, and a data processing unit 600. The multicolor fluorescence analysis device 12 is different from that in the first embodiment in terms of the types of the transmission filter 557 in the optical unit 502. In the optical unit 502, the same components are denoted by the same reference numerals as those of the above-described embodiment, and the detailed description thereof will be omitted.

Figure 9:
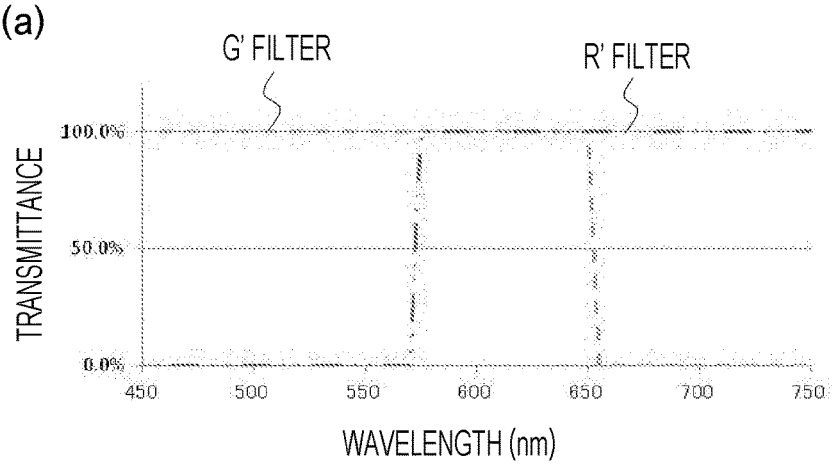
FIG. 9 is a schematic view illustrating wavelength characteristics in a multicolor fluorescence analysis device according to a second embodiment of the present invention, in which (a) illustrates a wavelength characteristic (transmittance) of a transmission filter, and (b) illustrates an intensity ratio of each fluorescent dye for each transmission filter.

FIG. 9(a) is a schematic view illustrating a wavelength characteristic (transmittance) of the transmission filter in the multicolor fluorescence analysis device according to the second embodiment of the present invention. In this embodiment, as illustrated in FIG. 9(a), the types of the transmission filters 557 is configured with two types (one is a G' filter and the other is an R' filter (refer to FIG. 10)). The G' filter has a transmission region in a range of approximately 450 nm to 650 nm and the R' filter has a transmission region in a range of approximately 575 nm to 750 nm.

Herein, the intensity ratio of the fluorescence emitted from each of the fluorescent dyes detected by the detection elements corresponding to the G' filter and the R' filter are calculated by using the integral value of the spectrum obtained by superposing the fluorescence spectrum of FIG. 7A (d) and the transmittance of each of various transmission filters 557 illustrated in FIG. 9(a). The result is illustrated in FIG. 9(b). As illustrated in FIG. 9(b), since the ratio of the signal intensities detected by the G' filter and the R' filter differs according to each fluorescent dye, it is possible to identify the fluorescent dyes from the ratio.

Figure 10:
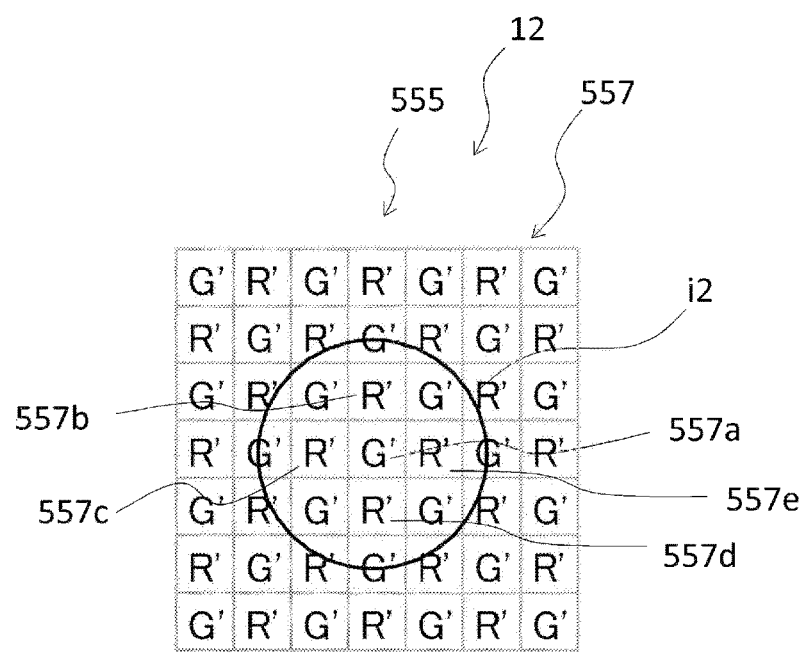
FIG. 10 is a schematic view illustrating an example of an image of DNA beads formed on a two-dimensional image sensor in the second embodiment.

FIG. 10 is a schematic view illustrating an example of an image i2 of the DNA beads formed on the two-dimensional image sensor in the second embodiment. This figure illustrates an example where the imaging magnification of the optical unit 502 is about 13.3 times, the size of the detection element of the two-dimensional image sensor is 3 μm, and the projection size of the DNA beads is 0.9 μm in diameter (however, in the figure, the influence of aberration and imaging ability of the optical system are not considered). In this case, for example, as illustrated in the following procedures (1) to (3), the fluorescent dyes can be identified.

(1) A filter (G' filter or R' filter) having the highest intensity is extracted from the region where the DNA beads are displayed in the two-dimensional image sensor. For example, in FIG. 10, a G' filter 557a is extracted.

(2) According to the average of the intensities of the different types of detection elements (R' filters 557b, 557c, 557d, and 557e in FIG. 10) adjacent to the filter extracted in the above-described (1) or a special approximate calculation method, the intensities of the different types of detection elements (R' filters) in (1) is estimated.

(3) The ratios of the intensities of different types of detection elements (R' filter) obtained in the above-described (2) and the ratio of the filter (G' filter 557a) extracted in the above-described (1) are calculated, and the obtained ration is compared with the ratios of the G' filter and R' filter described in FIG. 9(b) to identify the fluorescent dyes bound to the DNA beads.

In this manner, since the transmission filters 557 are of two types, the number of detection elements to be allocated to one DNA bead can be reduced in comparison with a case where the above-described transmission filter 556 is of four types. As a result, the multicolor fluorescence analysis device 12 can increase the detectable area at once by decreasing the imaging magnification and can improve the throughput of deciphering the base sequence by increasing the number of measurable samples s.

Third Embodiment

A multicolor fluorescence analysis device 13 according to a third embodiment is schematically configured to include a flow cell 100, a reagent container 200, a transport unit 300, a liquid feeding unit 400, an optical unit 503, and a data processing unit 600. The multicolor fluorescence analysis device 13 is different from that in the first embodiment in terms of the excitation filter 525 and the transmission filter 557 in the optical unit 503. In the optical unit 503, the same components are denoted by the same reference numerals as those of the above-described embodiments, and the detailed description thereof will be omitted.

In the multicolor fluorescence analysis device 13 according to the embodiment, the optical unit 503 is configured to include an irradiation optical unit having a plurality of switchable excitation filters that transmit light in a plurality of different excitation wavelength bands and irradiate the sample light emitted from a light source through an excitation filter as excitation light.

Figure 11:
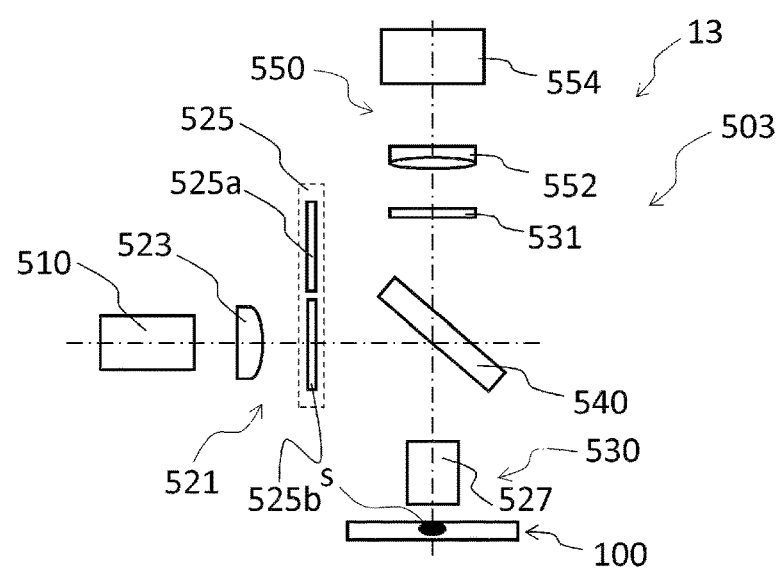
FIG. 11 is a schematic front view illustrating an example of an optical unit of a multicolor fluorescence analysis device according to a third embodiment of the present invention.

FIG. 11 is a schematic front view illustrating an example of the optical unit of the multicolor fluorescence analysis device according to the third embodiment of the present invention. In the multicolor fluorescence analysis device 13, as illustrated in FIG. 11, the excitation filter 525 is configured to include a first excitation filter 525a and a second excitation filter 525b.

In the embodiment, the dichroic mirror 540 has characteristic of reflecting all or some of the wavelength bands transmitted by the first excitation filter 525a and the second excitation filter 525b and transmitting all or some of the wavelength bands transmitted by the fluorescence filter 531.

Figure 12:
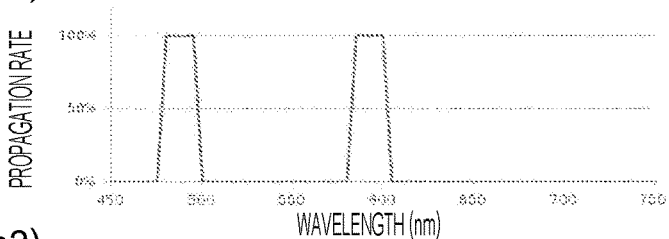
FIG. 12 is a schematic view illustrating wavelength characteristics of the multicolor fluorescence analysis device of FIG. 11, in which (a1) illustrates a wavelength characteristic (propagation rate) obtained by superposing a first excitation filter and a dichroic mirror, (a2) illustrates a wavelength characteristic (propagation rate) obtained by superposing a second excitation filter and a dichroic mirror, (b) illustrates a wavelength characteristic (transmittance) obtained by superposing a dichroic mirror and a fluorescence filter, (c1) illustrates an intensity ratio of each fluorescent dye for each transmission filter in the case of using the first excitation filter, and (c2) illustrates an intensity ratio of each fluorescent dye for each transmission filter in the case of using the second excitation filter.
Figure 12:
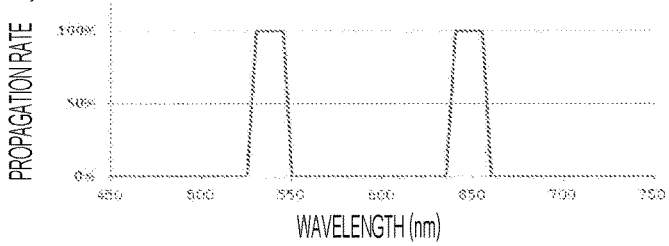
Figure 12:
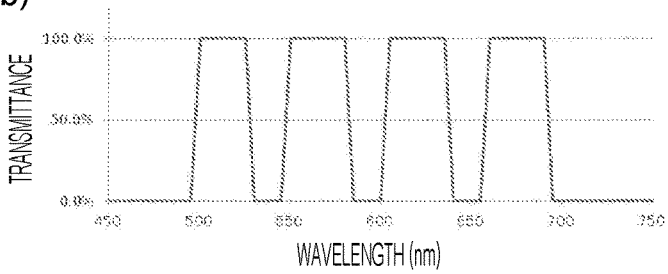

In addition, FIG. 12(a1) illustrates a wavelength characteristic (propagation rate) of the excitation light irradiated on the sample s by using the first excitation filter 525a and the dichroic mirror 540, and FIG. 12(a2) illustrates a wavelength characteristic (propagation rate) of the second excitation light irradiated on the sample s by using the excitation filter 525b and the dichroic mirror 540. In addition, FIG. 12(b) illustrates a wavelength characteristic (transmittance) obtained by superposing the dichroic mirror 540 and the fluorescence filter 531.

Next, in the third embodiment, a method of identifying the fluorescent dyes contained in the sample s will be described. In the following description, it is assumed that the dichroic mirror 540 reflects light in wavelength bands transmitted by the first and second excitation filters 525a and 525b with an efficiency of 100% and transmits light in a wavelength band transmitted by the fluorescence filter 531 with a probability of 100%. For the convenience, it is assumed that the characteristics (for example, characteristics of a spectrum of the light source 510, a spectral sensitivity of each detection element in the two-dimensional detector 554, and the like) other than the optical elements are uniform in a wavelength range to be detected.

First, if the fluorescence measurement is performed in the state where the first excitation filter 525a is inserted into the optical axis, the first fluorescent dye and the third fluorescent dye are mainly excited, and in the two-dimensional detector 554, the fluorescence from each of the fluorescent dyes is detected with the signal ratio (intensity ratio) illustrated in FIG. 12(c1). Although the second fluorescent dye and the fourth fluorescent dye also emit some fluorescence, since the intensities of the fluorescence are weak, the intensities of the fluorescence are excluded from the objects of the analysis by using the filtering function on the basis of the signal intensities detected by the two-dimensional image sensor (camera).

Next, if the fluorescence measurement is performed in the state where the second excitation filter 525b is inserted into the optical axis, the second fluorescent dye and the fourth fluorescent dye are mainly excited, and in the two-dimensional detector 554, the fluorescence from each of the fluorescent dyes is detected with the signal ratio (intensity ratio) illustrated in FIG. 12(c2). Although the first fluorescent dye and the third fluorescent dye also emit some fluorescence, since the intensities of the fluorescence are weak, the intensities of the fluorescence are excluded from the objects of the analysis by using the filtering function on the basis of the signal intensities detected by the two-dimensional image sensor (camera).

At that time, the first fluorescent dye and the third fluorescent dye are identified from the intensity ratios in the G' filter and the R' filter obtained by using the first excitation filter 525a, and the first and third fluorescent dyes are simultaneously identified. On the other hand, the second fluorescent dye and the fourth fluorescent dye are identified from the intensity ratios in the G' filter and the R' filter (refer to FIG. 10) obtained by using the second excitation filter 525b, and the second and fourth fluorescent dyes are simultaneously identified. By doing so, the first to fourth fluorescent dyes in each sample s can be identified, and thus, the base sequence of the DNA fragment can be deciphered.

In this manner, since the irradiation optical unit 521 has a plurality of switchable excitation filters 525 that transmit light in a plurality of different excitation wavelength bands, the number of fluorescent dyes to be simultaneously detected can be reduced by one excitation filter (each of the first excitation filter 525a and the second excitation filter 525b), so that it is possible to improve the color separation performance and to more reliably identify the fluorescent dyes.

Fourth Embodiment

A multicolor fluorescence analysis device 14 according to a fourth embodiment is schematically include a flow cell 100, a reagent container 200, a transport unit 300, a liquid feeding unit 400, an optical unit 504, and a data processing unit 600. The multicolor fluorescence analysis device 14 is different from that in the first embodiment in terms of the light source and the excitation filter in the optical unit 504. In the optical unit 504, the same components are denoted by the same reference numerals as those of the above-described embodiments, and the detailed description thereof will be omitted.

In the multicolor fluorescence analysis device 14 according to the embodiment, the optical unit 504 is configured to include a plurality of light sources for excitation and an irradiation optical unit having excitation filters that are provided for the respective light sources and transmit light having a plurality of different excitation wavelength bands and irradiate the sample with light emitted from the light sources through the excitation filters as excitation light.

Figure 13:
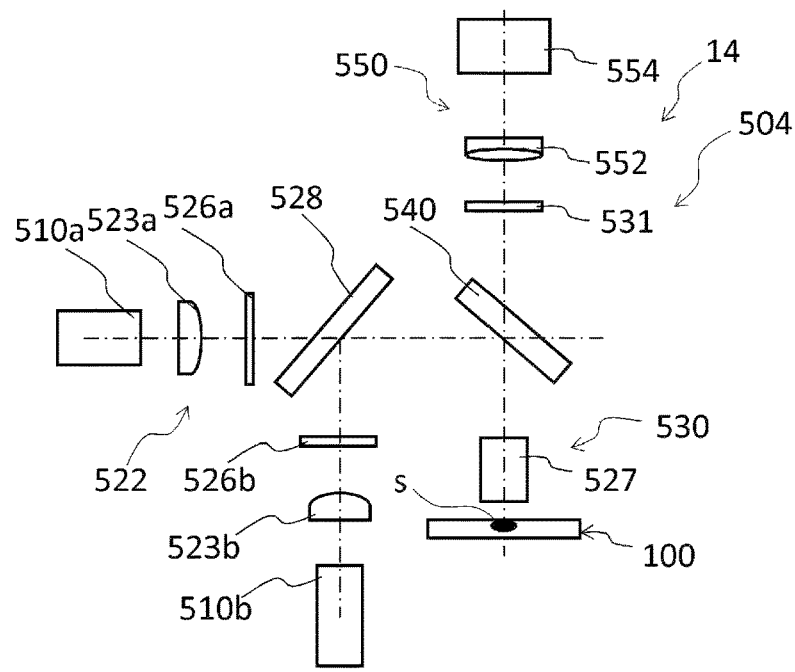
FIG. 13 is a schematic front view illustrating an example of an optical unit in a multicolor fluorescence analysis device according to a fourth embodiment of the present invention.

FIG. 13 is a schematic front view illustrating an example of an optical unit in the multicolor fluorescence analysis device 14 according to the fourth embodiment of the present invention. In the multicolor fluorescence analysis device 14, as illustrated in FIG. 13, the irradiation optical unit 522 is configured to include a first light source 510*a*, a first collimating lens 523*a*, a first excitation filter 526*a*, a second light source 510*b*, a second collimating lens 523*b*, a second excitation filter 526*b*, and an excitation dichroic mirror 528.

The first and second light sources 510*a* and 510*b* have the same configuration as that of the light source 510 in the first embodiment. In addition, the first and second collimating lenses 523*a* and 523*b* have the same configuration as that of the collimating lens 523 in the first embodiment.

The first excitation filter 526*a* is a filter that transmits light in a wavelength band that excites the first fluorescent dye and the third fluorescent dye. The second excitation filter 526*b* is a filter that transmits light in a wavelength band that excites the second fluorescent dye and the fourth fluorescent dye. The first and second excitation filters 526*a* and 526*b* have different wavelength characteristics with respect to wavelength.

The excitation dichroic mirror 528 is a mirror that transmits the excitation light transmitted by the first excitation filter 526*a* and reflects the excitation light transmitted by the second excitation filter 526*b*. By the excitation dichroic mirror 528, the optical axis of the light emitted from the first light source 510*a* and the optical axis of the light emitted from the second light source 510*b* can be coincident with each other.

In addition, the wavelength characteristics (propagation rate) of the excitation light irradiated on the samples by using the first light source 510*a* and the second light source 510*b* are similar to those in FIGS. 12(*a*1) and 12(*a*2), respectively.

In addition, in the multicolor fluorescence analysis device 14 according to the embodiment, the first light source 510*a* and the second light source 510*b* are alternately turned on. By turning on the first light source 510*a*, the first fluorescent dye and the third fluorescent dye are simultaneously identified, and by turning on the second light source 510*b*, the second fluorescent dye and the fourth fluorescent dye are simultaneously identified (identification of the first and third fluorescent dyes and identification of the second and fourth fluorescent dyes are separately performed).

In this manner, a plurality of the light sources 510*a* and 510*b* for excitation and the irradiation optical unit 522 that is provided for each light source and has the excitation filters 526*a* and 526*b* that transmit the light in a plurality of different excitation wavelength bands are provided, so that it is possible to more reliably identify the fluorescent dyes by improving the color separation performance similarly to the above-described third embodiment, and due to the absence of mechanical switching of the excitation filters 526*a* and 526*b*, it is possible to avoid occurrence of trouble of the device caused by any mechanical operation, so that it is expected to extend the lifetime of the device.

Fifth Embodiment

A multicolor fluorescence analysis device 15 according to a fifth embodiment is schematically configured to include a flow cell 100, a reagent container 200, a transport unit 300, a liquid feeding unit 400, an optical unit 505, and a data processing unit 600. The multicolor fluorescence analysis device 15 is different from that of the first embodiment in terms of the splitting unit and the two-dimensional detection unit in the optical unit 505. In addition, in the optical unit 505, the same components are denoted by the same reference numerals as those of the above-described embodiments, and the detailed description thereof will be omitted.

Figure 14:
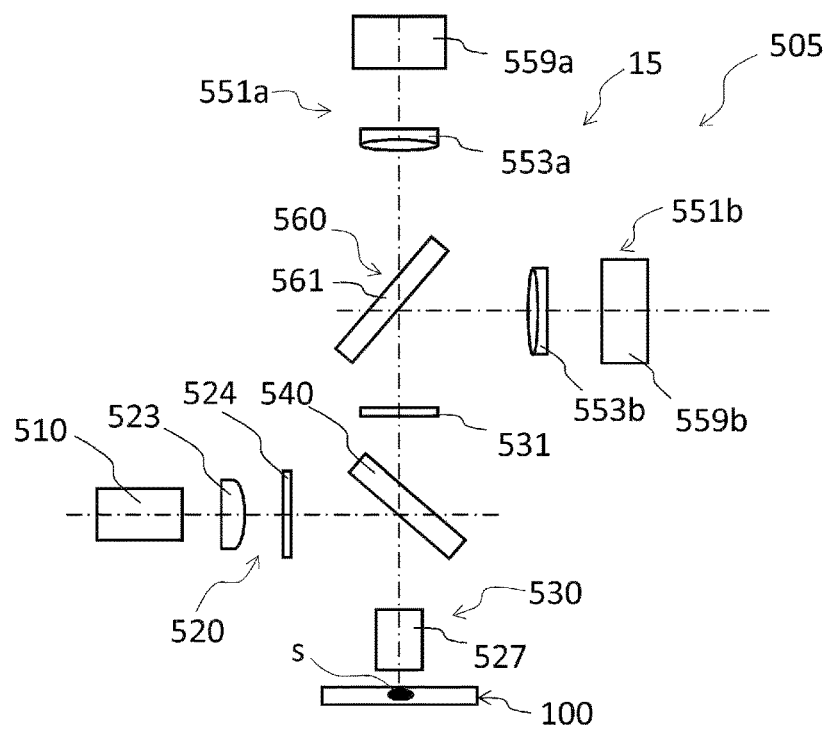
FIG. 14 is a schematic front view illustrating an example of an optical unit in a multicolor fluorescence analysis device according to a fifth embodiment of the present invention.

FIG. 14 is a schematic front view illustrating an example of the optical unit in the multicolor fluorescence analysis device 15 according to the fifth embodiment. As illustrated in FIG. 14, in the multicolor fluorescence analysis device 15, the optical unit 505 is configured to include a splitting unit 560 that splits the light transmitted by the fluorescence filter 531 into two at a predetermined ratio for each wavelength. Specifically, the splitting unit 560 has a dichroic mirror that transmits a portion of the light transmitted by the fluorescence filter 531 and reflects the remaining portion. In the embodiment, the dichroic mirror is configured by a splitting dichroic mirror 561. The splitting dichroic mirror 561 has such a characteristic that transmittance (reflectance) thereof changes substantially from 0% to 100% with respect to a predetermined wavelength range.

Figure 15:
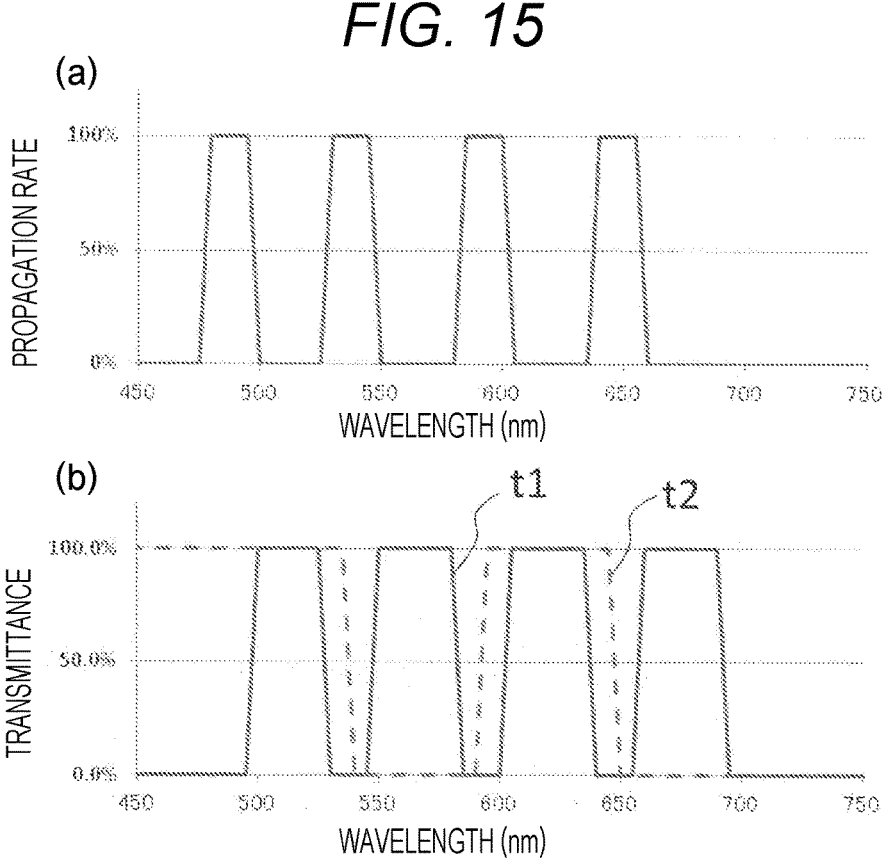
FIG. 15 is a schematic view illustrating wavelength characteristics in the fifth embodiment, in which (a) illustrates a wavelength characteristic (propagation rate) obtained by superposing an excitation filter and a dichroic mirror, and (b) illustrates a wavelength characteristic (transmittance) of a splitting unit.

FIG. 15(*a*) illustrates a wavelength characteristic (propagation rate) of the excitation light irradiated on the sample s by using the excitation filter 524 and the dichroic mirror 540. FIG. 15(*b*) is a schematic view illustrating a wavelength characteristic (transmittance) of the splitting unit 560. The wavelength characteristic of the splitting dichroic mirror 561 has a wavelength characteristic indicated by a broken line t2 in FIG. 15(*b*) with respect to a wavelength characteristic (transmittance) obtained by superposing the dichroic mirror 540 indicated by a solid line t1 in FIG. 15(*b*) and the fluorescence filter 531.

The wavelength characteristic indicated by the broken line t2 in FIG. 15(*b*) is the transmittance of the splitting dichroic mirror 561. The transmittance of 0% denotes the reflectance of 100%, and the transmittance 100% denotes the reflectance of 0%. Namely, the transmittance and the reflectance have a relationship represented by the following formula (1).

$$\text{Reflectance (\%)}=100-\text{Transmittance (\%)} \quad (1)$$

Therefore, in the case of using the splitting dichroic mirror 561 having the wavelength characteristic illustrated in FIG. 15(*b*), the fluorescence emitted from the first and third fluorescent dyes is mainly transmitted by the splitting dichroic mirror 561 and is detected by the first two-dimensional detection unit 551*a*, and the fluorescence emitted from the second and fourth fluorescent dyes is mainly reflected by the splitting dichroic mirror 561 and is detected by the second two-dimensional detection unit 551*b*.

In this manner, the splitting unit 560 is the dichroic mirror, and the transmittance of the light transmitted by the dichroic mirror changes substantially from 0% to 100% with respect to a predetermined wavelength range, so that the light transmitted by the fluorescence filter 531 can be uniformly allocated, and thus, the fluorescent dyes can be more reliably identified.

In addition, as illustrated in FIG. 14, in the multicolor fluorescence analysis device 15, the optical unit 505 is configured to include the first two-dimensional detection unit 551*a* and the second two-dimensional detection unit 551*b*. The first two-dimensional detection unit 551*a* is configured to include a first tube lens 553*a* and a first two-dimensional detector 559*a*, and the second two-dimensional detection unit 551b is configured to include a second tube lens 553b and a second two-dimensional detector 559b.

The first tube lens 553a condenses the light transmitted by the splitting dichroic mirror 561 and forms an image on the two-dimensional image sensor of the first two-dimensional detector 559a described later. The first two-dimensional detector 559a has a plurality of types of first transmission filters that transmit light having a predetermined wavelength out of one of the two lights split by the splitting unit 560 and detects the intensity of the light having a predetermined wavelength for each of the first transmission filters. As a result, the fluorescent dyes are simultaneously identified from the fluorescence emitted from the first and third fluorescent dyes. In addition, since the first two-dimensional detector 559a is similar to that of the above-described second embodiment, the detailed description thereof will be omitted.

The second tube lens 553b condenses the light reflected by the splitting dichroic mirror 561 and forms an image on the two-dimensional image sensor of the second two-dimensional detector 559b described later. The second two-dimensional detector 559b has a plurality of types of second transmission filters that transmit light having a predetermined wavelength out of the other light split into two by the splitting unit 560 and detects the intensity of the light having a predetermined wavelength for each of the second transmission filters. As a result, the fluorescent dyes are simultaneously identified from the fluorescence emitted from the second and fourth fluorescent dyes. In addition, since the second two-dimensional detector 559b is similar to that of the above-described second embodiment, the detailed description thereof will be omitted.

In this manner, by providing the splitting unit 560 that splits the light transmitted by the fluorescence filter 531 into two at each predetermined ratio for each wavelength, it is possible to reduce the number of types of fluorescent dyes detected per two-dimensional detector, so that it is possible to improve the color separation performance and to more reliably identify the fluorescent dyes.

The present invention is not limited to the configuration of the above-described embodiments, but the present invention is defined by the scope of the Claims, and it is intended to include equivalents to the Claims and all changes within the scope.

For example, in the above-described first to fifth embodiments, each of the multicolor fluorescence analysis devices 11 to 15 is provided with the flow cell 100, the reagent container 200, the transport unit 300, the liquid feeding unit 400, the optical units 501 to 505, and the data processing unit 600. However, as long as the multicolor fluorescence analysis devices 11 to 15 can detect fluorescence emitted from a plurality of types of fluorescent dyes having different fluorescence wavelengths included in the sample by irradiation with excitation light, the multicolor fluorescence analysis devices are not particularly limited. For example, a multicolor fluorescence analysis device not provided with the flow cell 100, the reagent container 200, the transport unit 300, the liquid feeding unit 400, or the like is also intended to be within the scope of the present invention.

In addition, in the above-described embodiment, in the multicolor fluorescence analysis devices 11 to 15, the number of the excitation wavelength bands of the excitation light irradiated on the sample s is set to a specific number. However, a multicolor fluorescence analysis device may irradiate excitation light in excitation wavelength bands other than the specific number as long as the effect of the present invention is not impaired. The excitation light to be irradiated on the sample s is preferably configured with at least two excitation wavelength bands, more preferably configured with at least three excitation wavelength bands. Therefore, multicolor fluorescence can be simultaneously detected.

In the above-described embodiments, in the multicolor fluorescence analysis devices 11 to 15, the number of types of transmission filters is set to a specific number (for example, four types of transmission filters are provided in the first embodiment, and two types of transmission filters are provided in the second embodiment). However, a multicolor fluorescence analysis device may be provided with the number of types of transmission filters other than the specific number as long as the effect of the present invention is not impaired. Therefore, it is possible to appropriately select balance between a certainty in identification of fluorescent dyes and the measurable number of samples (throughput) per irradiation of excitation light.

INDUSTRIAL APPLICABILITY

The present invention can provide a multicolor fluorescence analysis device capable of quickly and reliably identifying fluorescence emitted from a plurality of types of fluorescent dyes having different fluorescence wavelengths. Therefore, the multicolor fluorescence analysis device can be appropriately used for fluorescence analysis of living body-related substances such as DNAs and RNAs labeled with fluorescent dyes.

REFERENCE SIGNS LIST s sample
11 to 15 multicolor fluorescence analysis device
100 flow cell
200 reagent container
300 transport unit
400 liquid feeding unit
501 to 505 optical unit
600 data processing unit
510 light source
520 to 522 irradiation optical unit
524 excitation filter
526a first excitation filter
526b second excitation filter
530 fluorescence condensation unit
531 fluorescence filter
540 dichroic mirror
550 two-dimensional detection unit
554, 555 two-dimensional detector
556, 557 transmission filter
559a first two-dimensional detector
559b second two-dimensional detector
560 splitting unit

The invention claimed is:
1. A multicolor fluorescence analysis device for detecting fluorescence emitted from a plurality of types of fluorescent dyes having different fluorescence wavelengths contained in a sample by irradiation with excitation light, the multicolor fluorescence analysis device comprising:
    a light source for excitation;
    an irradiation optical unit having an excitation filter that transmits light in a plurality of different excitation wavelength bands and irradiating the sample with light emitted from the light source as the excitation light through the excitation filter;

a fluorescence condensation unit having a fluorescence filter that transmits at least a portion of the fluorescence emitted from the sample by the irradiation of the excitation light and transmits light in a plurality of transmission wavelength bands not including the excitation wavelength band; and a two-dimensional detector having a plurality of types of transmission filters that transmit light having a predetermined wavelength out of the light transmitted by the fluorescence filter and a two-dimensional sensor configured to detect an intensity of the light transmitted by each of the transmission filters for each of the transmission filters, the plurality of types of transmission filters being provided to each detection element of the two-dimensional sensor so to correspond to each detection element, wherein light emitted from at least two types of fluorescent dyes out of the plurality of types of fluorescent dyes is simultaneously detected by using the two-dimensional detector, and the types of the fluorescent dyes are identified from intensities of the detected light, and the transmission filters are configured with four types having different transmission wavelength bands.

2. The multicolor fluorescence analysis device according to claim 1, wherein the four types of transmission filters are arranged by setting a block where the respective types of transmission filters are aligned one by one as one unit and repeating the unit in a plane direction.

3. The multicolor fluorescence analysis device according to claim 1, wherein the fluorescent dyes are of four types, and intensity ratios of fluorescence from the fluorescent dyes are different among the respective transmission filters.

4. The multicolor fluorescence analysis device according to claim 3,
wherein the four types of fluorescent dyes are a first dye, a second dye, a third dye, and a fourth dye, and the four types of transmission filters are a first filter, a second filter, a third filter, and a fourth filter,
each of the fluorescence from the first dye and the fluorescence from the second dye has the highest intensity ratio in the first filter,
in the second filter, the intensity ratio of the fluorescence from the first dye is larger than the intensity ratio of the fluorescence from the second dye,
each of the fluorescence from the third dye and the fluorescence from the fourth dye has the highest intensity ratio in the third filter, and
in the fourth filter, the intensity ratio of the fluorescence from the fourth dye is larger than the intensity ratio of the fluorescence from the third dye.

5. The multicolor fluorescence analysis device according to claim 1, wherein the excitation light to be irradiated on the sample is configured with at least two excitation wavelength bands.

6. The multicolor fluorescence analysis device according to claim 1, wherein the excitation light to be irradiated on the sample is configured with at least three excitation wavelength bands.

7. The multicolor fluorescence analysis device according to claim 1, further comprising a data processing unit identifying two or more types of fluorescent dyes from the intensity of light detected by the two-dimensional detector.

8. A multicolor fluorescence analysis device for detecting fluorescence emitted from a plurality of types of fluorescent dyes having different fluorescence wavelengths contained in a sample by irradiation with excitation light, the multicolor fluorescence analysis device comprising:
a light source for excitation;
an irradiation optical unit having a plurality of excitation filters that transmit light in a plurality of different excitation wavelength bands and are switchable and irradiating the sample with light emitted from the light source as the excitation light through the excitation filter;
a fluorescence condensation unit having a fluorescence filter that transmits at least a portion of the fluorescence emitted from the sample by the irradiation of the excitation light and transmits light in a plurality of transmission wavelength bands not including the excitation wavelength band; and
a two-dimensional detector having a plurality of types of transmission filters that transmit light having a predetermined wavelength out of the light transmitted by the fluorescence filter and a two-dimensional sensor configured to detect an intensity of the light transmitted by each of the transmission filters for each of the transmission filters, the plurality of types of transmission filters being provided to each detection element of the two-dimensional sensor so to correspond to each detection element,
wherein light emitted from at least two types of fluorescent dyes out of the plurality of types of fluorescent dyes is simultaneously detected by using the two-dimensional detector, and the types of the fluorescent dyes are identified from intensities of the detected light, and
the transmission filters are configured with four types having different transmission wavelength bands.

9. The multicolor fluorescence analysis device according to claim 8, wherein the four types of transmission filters are arranged by setting a block where the respective types of transmission filters are aligned one by one as one unit and repeating the unit in a plane direction.

10. The multicolor fluorescence analysis device according to claim 8, wherein the fluorescent dyes are of four types, and intensity ratios of fluorescence from the fluorescent dyes are different among the respective transmission filters.

11. The multicolor fluorescence analysis device according to claim 10, wherein the four types of fluorescent dyes are a first dye, a second dye, a third dye, and a fourth dye, and the four types of transmission filters are a first filter, a second filter, a third filter, and a fourth filter,
each of the fluorescence from the first dye and the fluorescence from the second dye has the highest transmittance in the first filter,
in the second filter, the intensity ratio of the fluorescence from the first dye is larger than the intensity ratio of the fluorescence from the second dye,
each of the fluorescence from the third dye and the fluorescence from the fourth dye has the largest intensity ratio in the third filter, and
in the fourth filter, the intensity ratio of fluorescence from the fourth dye is larger than the intensity ratio of fluorescence from the third dye.

12. A multicolor fluorescence analysis device for detecting fluorescence emitted from a plurality of types of fluorescent dyes having different fluorescence wavelengths contained in a sample by irradiation with excitation light, the multicolor fluorescence analysis device comprising:
a plurality of light sources for excitation;
an irradiation optical unit having an excitation filter that is provided for each of the light sources to transmit light in a plurality of different excitation wavelength bands and irradiating the sample with light emitted from the light source as the excitation light through the excitation filter;
a fluorescence condensation unit having a fluorescence filter that transmits at least a portion of the fluorescence emitted from the sample by the irradiation of the excitation light and transmits light in a plurality of transmission wavelength bands not including the excitation wavelength band; and
a two-dimensional detector having a plurality of types of transmission filters that transmit light having a predetermined wavelength out of the light transmitted by the fluorescence filter and a two-dimensional sensor configured to detect an intensity of the light transmitted by each of the transmission filters for each of the transmission filters, the plurality of types of transmission filters being provided to each detection element of the two-dimensional sensor so to correspond to each detection element,
wherein one of the plurality of light sources is turned on to simultaneously detect light emitted from at least two types of fluorescent dyes out of the plurality of types of fluorescent dyes by using the two-dimensional detector, and the types of the fluorescent dyes are identified from intensities of the detected light, and
the transmission filters are configured with four types having different transmission wavelength bands.

13. The multicolor fluorescence analysis device according to claim 12, wherein the four types of transmission filters are arranged by setting a block where the respective types of transmission filters are aligned one by one as one unit and repeating the unit in a plane direction.

14. The multicolor fluorescence analysis device according to claim 12, wherein the fluorescent dyes are of four types, and intensity ratios of fluorescence from the fluorescent dyes are different among the respective transmission filters.

15. The multicolor fluorescence analysis device according to claim 14,
wherein the four types of fluorescent dyes are a first dye, a second dye, a third dye, and a fourth dye, and the four types of transmission filters are a first filter, a second filter, a third filter, and a fourth filter,
each of the fluorescence from the first dye and the fluorescence from the second dye has the highest intensity ratio in the first filter,
in the second filter, the intensity ratio of the fluorescence from the first dye is larger than the intensity ratio of the fluorescence from the second dye,
each of the fluorescence from the third dye and the fluorescence from the fourth dye has the highest intensity ratio in the third filter, and
in the fourth filter, the intensity ratio of the fluorescence from the fourth dye is larger than the intensity ratio of the fluorescence from the third dye.

16. A multicolor fluorescence analysis device for detecting fluorescence emitted from a plurality of types of fluorescent dyes having different fluorescence wavelengths contained in a sample by irradiation with excitation light, the multicolor fluorescence analysis device comprising:
a light source for excitation;
an irradiation optical unit having an excitation filter that transmits light in a plurality of different excitation wavelength bands and irradiating the sample with light emitted from the light source as the excitation light through the excitation filter;
a fluorescence condensation unit having a fluorescence filter that transmits at least a portion of the fluorescence emitted from the sample by the irradiation of the excitation light and transmits light in a plurality of transmission wavelength bands not including the excitation wavelength band;
a dichroic mirror splitting the light transmitted by the fluorescence filter into two at a predetermined ratio for each of the transmission wavelength bands;
a first two-dimensional detector having a plurality of types of first transmission filters that transmit light having a predetermined wavelength out of one of the two lights split by the splitting unit and a first two-dimensional sensor configured to detect an intensity of the light transmitted by each of the first transmission filters for each of the first transmission filters, the plurality of types of first transmission filters being provided to each detection element of the first two-dimensional sensor so to correspond to each detection element of the first two-dimensional sensor; and
a second two-dimensional detector having a plurality of types of second transmission filters that transmit light having a predetermined wavelength out of the other of the two lights split by the splitting unit and a second two-dimensional sensor configured to detect an intensity of the light transmitted by each of the second transmission filters for each of the second transmission filters, the plurality of types of second transmission filters being provided to each detection element of the second two-dimensional sensor so to correspond to each detection element of the second two-dimensional sensor,
wherein light emitted from at least two types of fluorescent dyes out of the plurality of types of fluorescent dyes is simultaneously detected by using the first and second two-dimensional detectors, and the types of the fluorescent dyes are identified from intensities of the detected light.

17. The multicolor fluorescence analysis device according to claim 16, wherein the types of the first and second transmission filters are four types, respectively.

18. The multicolor fluorescence analysis device according to claim 16, wherein the types of the first and second transmission filters are two types, respectively.

19. The multicolor fluorescence analysis device according to claim 16, wherein the dichroic mirror that transmits a portion of the light transmitted by the fluorescence filter and reflects the remaining portion, and transmittance of the light transmitted by the dichroic mirror changes substantially from 0% to 100% in a predetermined wavelength range.

20. A multicolor fluorescence analysis device for detecting fluorescence emitted from a plurality of types of fluorescent dyes having different fluorescence wavelengths contained in a sample by irradiation with excitation light, the multicolor fluorescence analysis device comprising:
a light source for excitation;
an irradiation optical unit having an excitation filter that transmits light in a plurality of different excitation wavelength bands and irradiating the sample with the light emitted from the light source as excitation light through the excitation filter;
a fluorescence condensation unit having a fluorescence filter that transmits at least a portion of the fluorescence emitted from the sample by the irradiation of the excitation light and transmits light in a plurality of transmission wavelength bands not including the excitation wavelength band; and a two-dimensional detector having a plurality of types of transmission filters that transmit light having a predetermined wavelength out of the light transmitted by the fluorescence filter and a two-dimensional sensor configured to detect an intensity of the light transmitted by each of the transmission filters for each of the transmission filters, the plurality of types of transmission filters being provided to each detection element of the two-dimensional sensor so to correspond to each detection element, wherein light emitted from at least two types of fluorescent dyes out of the plurality of types of fluorescent dyes is simultaneously detected by using the two-dimensional detector, and the types of the fluorescent dyes are identified from intensities of the detected light, and the transmission filters are configured with two types having different transmission wavelength bands.

21. The multicolor fluorescence analysis device according to claim 20, wherein the fluorescent dyes are of four types, and intensity ratios of fluorescence from the fluorescent dyes are different among the respective transmission filters.

22. A multicolor fluorescence analysis device for detecting fluorescence emitted from a plurality of types of fluorescent dyes having different fluorescence wavelengths contained in a sample by irradiation with excitation light, the multicolor fluorescence analysis device comprising:

a light source for excitation;

an irradiation optical unit having a plurality of excitation filters that transmit light in a plurality of different excitation wavelength bands and are switchable and irradiating the sample with light emitted from the light source as the excitation light through the excitation filter;

a fluorescence condensation unit having a fluorescence filter that transmits at least a portion of the fluorescence emitted from the sample by the irradiation of the excitation light and transmits light in a plurality of transmission wavelength bands not including the excitation wavelength band; and a two-dimensional detector having a plurality of types of transmission filters that transmit light having a predetermined wavelength out of the light transmitted by the fluorescence filter and a two-dimensional sensor configured to detect an intensity of the light transmitted by each of the transmission filters for each of the transmission filters, the plurality of types of transmission filters being provided to each detection element of the two-dimensional sensor so to correspond to each detection element, wherein light emitted from at least two types of fluorescent dyes out of the plurality of types of fluorescent dyes is simultaneously detected by using the two-dimensional detector, and the types of the fluorescent dyes are identified from intensities of the detected light, and the transmission filters are configured with two types having different transmission wavelength bands.

23. The multicolor fluorescence analysis device according to claim 22, wherein the fluorescent dyes are of four types, and intensity ratios of fluorescence from the fluorescent dyes are different among the respective transmission filters.

24. A multicolor fluorescence analysis device for detecting fluorescence emitted from a plurality of types of fluorescent dyes having different fluorescence wavelengths contained in a sample by irradiation with excitation light, the multicolor fluorescence analysis device comprising:

a plurality of light sources for excitation;

an irradiation optical unit having an excitation filter that is provided for each of the light sources to transmit light in a plurality of different excitation wavelength bands and irradiating the sample with light emitted from the light source as the excitation light through the excitation filter;

a fluorescence condensation unit having a fluorescence filter that transmits at least a portion of the fluorescence emitted from the sample by the irradiation of the excitation light and transmits light in a plurality of transmission wavelength bands not including the excitation wavelength band; and a two-dimensional detector having a plurality of types of transmission filters that transmit light having a predetermined wavelength out of the light transmitted by the fluorescence filter and a two-dimensional sensor configured to detect an intensity of the light transmitted by each of the transmission filters for each of the transmission filters, the plurality of types of transmission filters being provided to each detection element of the two-dimensional sensor so to correspond to each detection element, wherein one of the plurality of light sources is turned on to simultaneously detect light emitted from at least two types of fluorescent dyes out of the plurality of types of fluorescent dyes by using the two-dimensional detector, and the types of the fluorescent dyes are identified from intensities of the detected light, and the transmission filters are configured with two types having different transmission wavelength bands.

25. The multicolor fluorescence analysis device according to claim 24, wherein the fluorescent dyes are of four types, and intensity ratios of fluorescence from the fluorescent dyes are different among the respective transmission filters.

* * * * *